United States Patent [19]

Reynolds

[11] Patent Number: 5,358,692

[45] Date of Patent: Oct. 25, 1994

[54] TISSUE CASSETTE HOLDER

[76] Inventor: Douglas W. Reynolds, 4499 Craig La., Vacaville, Calif. 95688

[21] Appl. No.: 114,929

[22] Filed: Sep. 2, 1993

[51] Int. Cl.⁵ .............................................. B01L 9/00
[52] U.S. Cl. ................................... 422/104; 422/99; 435/284; 435/299; 435/301; 435/310; 435/809; 206/558; 206/560; 206/564; 206/565; 206/569; 211/126; 211/194
[58] Field of Search ....................... 422/99, 102, 104; 435/284, 285, 287, 293, 299, 300, 301, 310, 809; 206/558, 564, 565, 560, 569; 211/126, 194

[56] References Cited

U.S. PATENT DOCUMENTS

| | | | |
|---|---|---|---|
| 3,696,921 | 10/1972 | Desmond | 206/565 X |
| 3,992,265 | 11/1976 | Hansen | 435/300 |
| 4,139,097 | 2/1979 | Bowman et al. | 206/560 X |
| 4,319,841 | 3/1982 | Suovaniemi et al. | 435/301 X |
| 4,421,246 | 12/1983 | Schultz et al. | 206/565 X |
| 4,549,670 | 10/1985 | Trendler | 220/338 |
| 4,557,903 | 12/1985 | McCormick | 422/102 X |
| 4,682,891 | 7/1987 | de Macario et al. | 356/244 |
| 4,801,553 | 1/1989 | Owen et al. | 422/99 X |
| 5,061,452 | 10/1991 | Yamamoto et al. | 435/301 X |
| 5,080,869 | 1/1992 | McCormick | 435/299 X |
| 5,269,671 | 12/1993 | McCormick | 422/99 X |
| 5,285,907 | 2/1994 | Franchere et al. | 211/74 |
| 5,290,521 | 3/1994 | DeStefano, Jr. | 422/99 |

Primary Examiner—Lyle A. Alexander
Assistant Examiner—Maureen M. Wallenhorst
Attorney, Agent, or Firm—Hugh E. Smith

[57] ABSTRACT

A tissue cassette holder including a rectangular open-top tray having a pair of locking side rails affixed to the upper portion of the longitudinal sides thereof, the rails having a raised elastomeric protuberance projecting inwardly from the center thereof and spaced sufficiently apart to permit a conventional tissue cassette to snap firmly therebetween. Preferably, the trays are configured to permit removably locking a plurality thereof into superposed and/or side-by-side relationship, and further to positively lock a plurality of cassettes within each such tray for liquid processing and to break such cassettes loose after the tray and cassettes are wax-dipped preparatory to slicing the tissue therein for microanalysis.

4 Claims, 4 Drawing Sheets

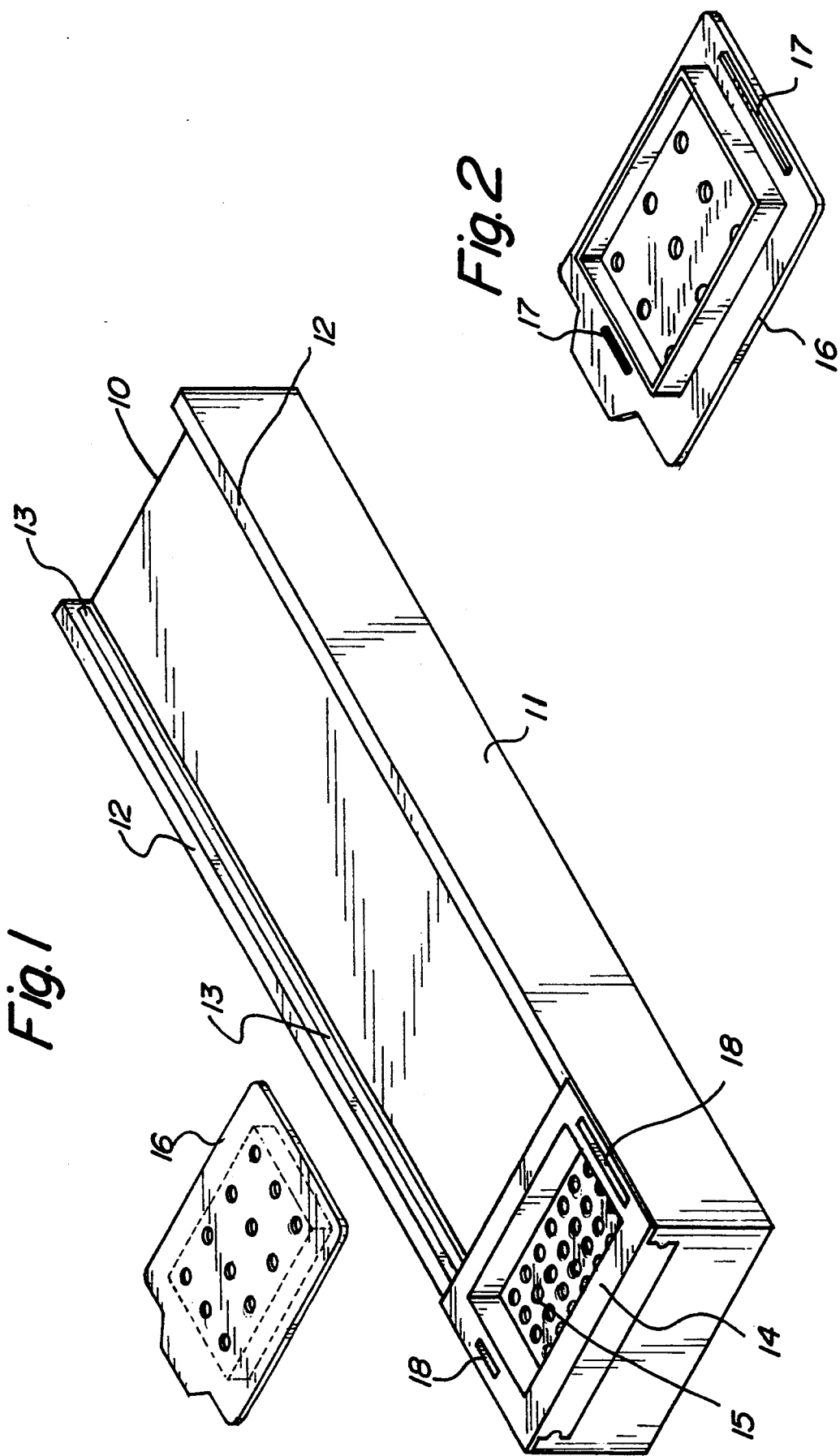

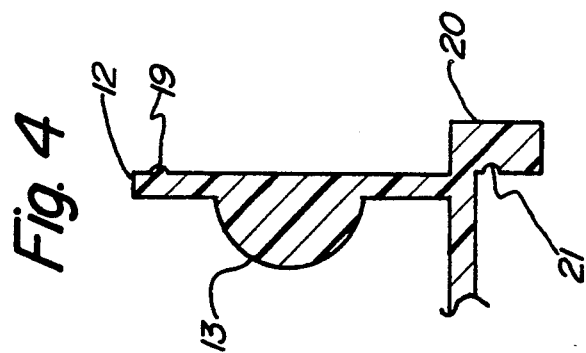
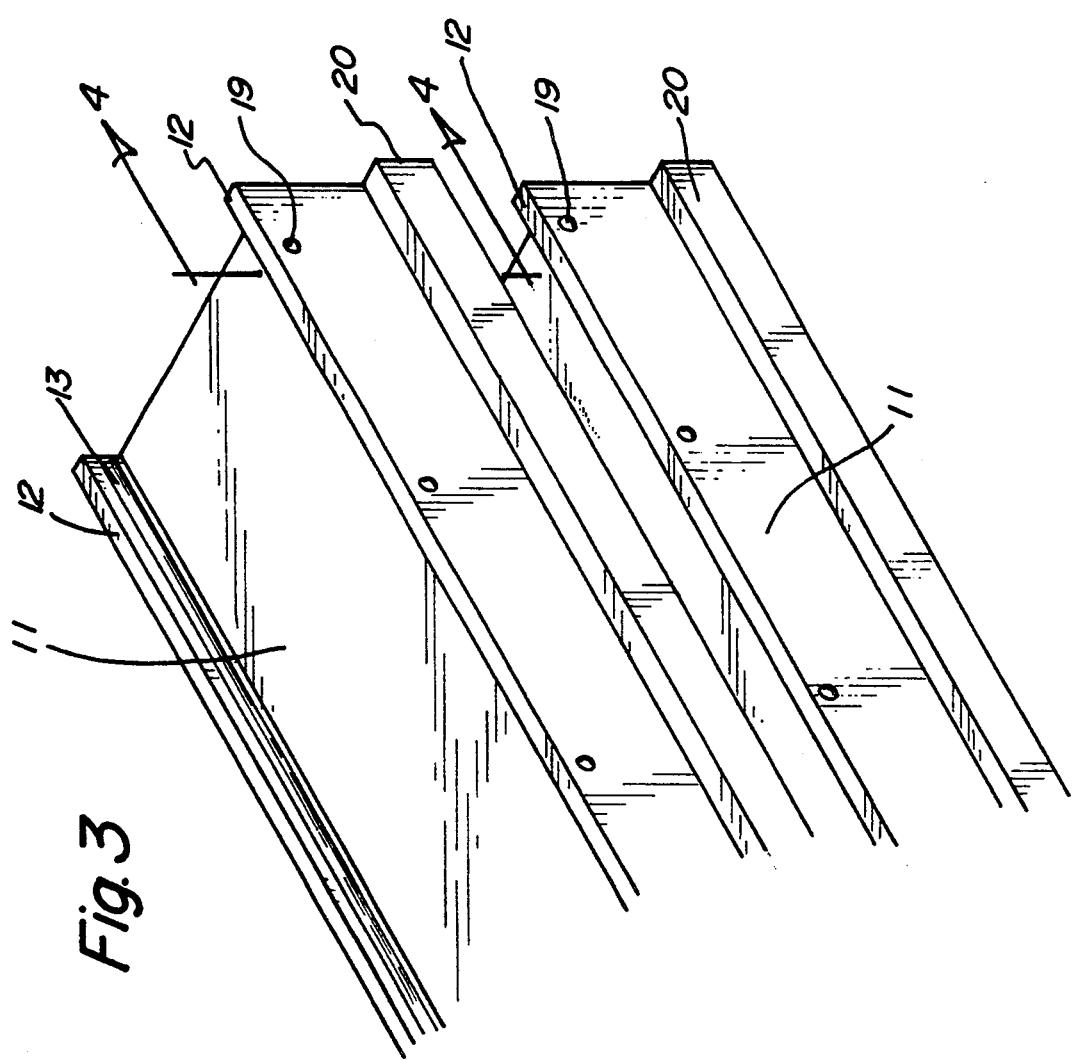

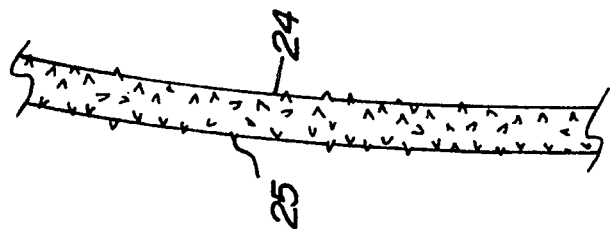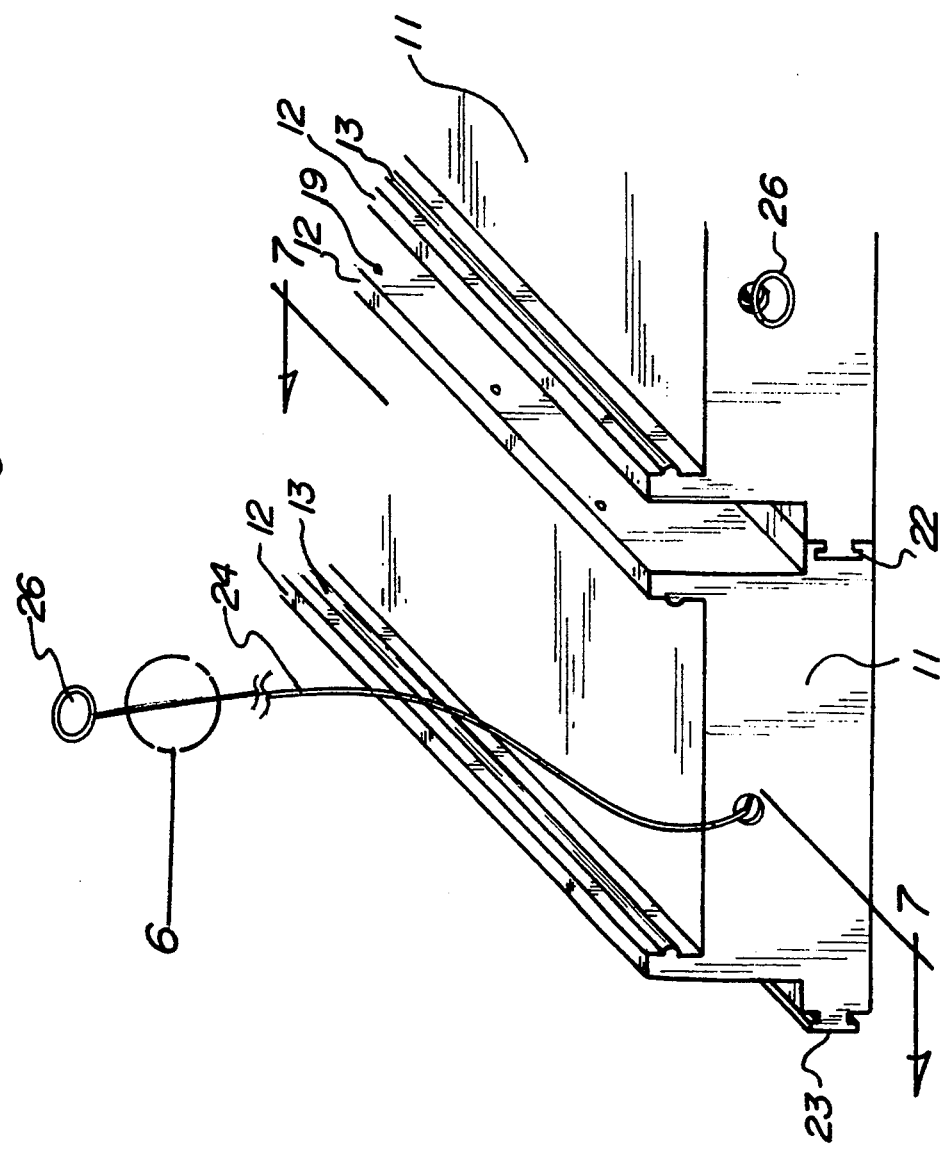

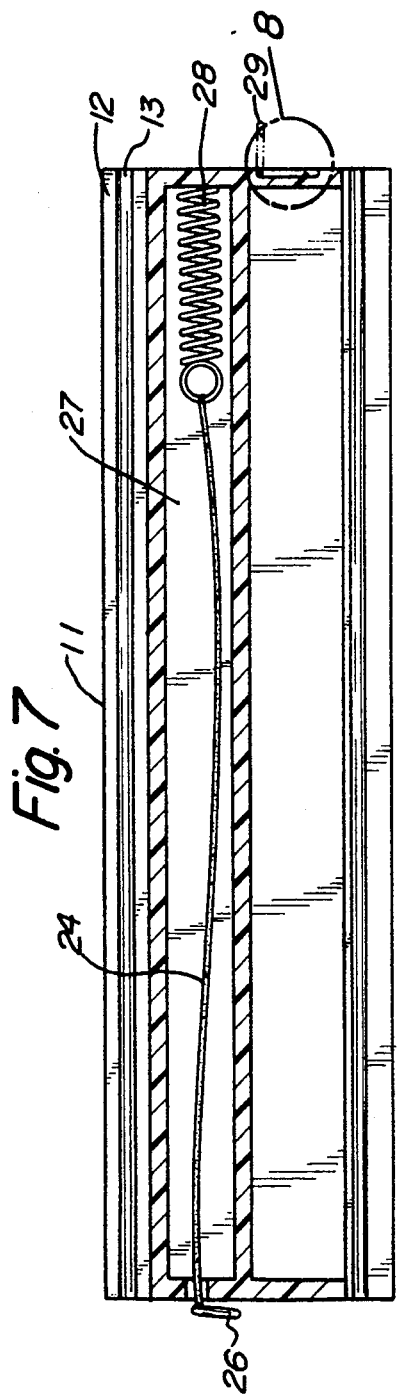
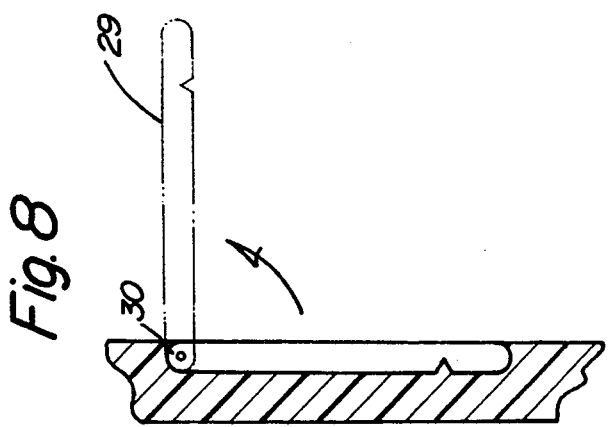

TISSUE CASSETTE HOLDER

BACKGROUND OF THE INVENTION

1. Field of the Invention

The present invention relates to tissue cassette holders and more particularly pertains to units which may be utilized to organize and store tissue cassettes prior to wax-dipping as a preliminary to slicing for microscopic examination.

2. Description of the Prior Art

The use of tissue cassettes is known in the prior art. More specifically, such cassettes heretofore devised and utilized for the purpose of holding tissue specimens are frequently scattered over work surfaces while being prepared where they may be dropped or even lost. Typical cassettes are shown in U.S. Pat. Nos. 4,421,246 and 4,549,670. U.S. Pat. No. 5,080,869 shows a tower-type stacking arrangement for tissue cassettes of a special design.

In this respect, the holder according to the present invention substantially departs from the conventional concepts and designs of the prior art, and in so doing provides an apparatus primarily developed for the purpose of organizing and holding conventional tissue cassettes during processing until they have been wax-dipped in preparation for microanalysis.

Therefore, it can be appreciated that there exists a continuing need for new and improved means which can be utilized to organize and store tissue cassettes. In this regard, the present invention substantially fulfills this need.

SUMMARY OF THE INVENTION

In view of the foregoing disadvantages inherent in the known types of tissue cassette handling means now present in the prior art, the present invention provides an improved tissue cassette holder construction wherein the same can be utilized to organize and store conventional cassettes throughout preparation steps for microscopic analysis. As such, the general purpose of the present invention, which will be described subsequently in greater detail, is to provide a new and improved tissue cassette storing device which has all the advantages of the prior art devices and none of the disadvantages.

To attain this, the present invention essentially relates to a tissue cassette holder which comprises a rectangular open-top tray having a pair of locking side rails affixed to the upper portion of the longitudinal sides thereof, said rails having a raised elastomeric protuberance projecting inwardly from the center thereof and spaced sufficiently apart to permit a conventional tissue cassette to snap firmly therebetween. Preferably, means are provided on such trays to permit removably locking a plurality thereof into superposed and/or side-by-side relationship, and further means to positively lock a plurality of cassettes within each such tray for liquid processing and to function to break such cassettes loose after the tray and cassettes are wax-dipped preparatory to slicing the tissue therein for microanalysis.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved tissue cassette holder which has all the advantages of the prior art holders and none of the disadvantages.

It is another object of the present invention to provide a new and improved tissue cassette holder which may be easily and efficiently manufactured and marketed.

It is a further object of the present invention to provide a new and improved tissue cassette holder which is of a durable and reliable construction.

An even further object of the present invention is to provide a new and improved tissue cassette holder which is susceptible of a low cost of manufacture with regard to both materials and labor, and which accordingly is then susceptible of low prices of sale to the consuming public, thereby making such holders economically available to the buying public.

Still another object of the present invention is to provide a new and improved device for organizing and storing tissue cassettes during processing.

Yet another object of the present invention is to provide a new and improved tissue cassette holder which will organize and hold such cassettes during processing, including wax-dipping, and will then permit easy removal of such cassettes for storage or further use.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a holder of the present invention.

FIG. 2 is a perspective view of a perforate conventional tissue cassette.

FIG. 3 is a perspective view of holders of the present invention illustrating means for stacking such holders together.

FIG. 4 is a sectional view on line 4—4 of FIG. 3.

FIG. 5 is a perspective view showing means for engaging the trays of the present invention in side-to-side relationship as well as the means for positively fastening cassettes within such trays.

FIG. 6 is a perspective view of the cable shown in FIG. 5 in an enlargement of the area shown as "6" in FIG. 5.

FIG. 7 is a top plan view of a holder of the present invention showing details of the cassette holding means.

FIG. 8 is a side plan view (enlarged) of the area shown at "8" in FIG. 7.

DESCRIPTION OF THE PREFERRED EMBODIMENT

With reference now to the drawings, and in particular to FIG. 1 thereof, a new and improved tissue cassette holder embodying the principles and concepts of the present invention and generally designated by the reference numeral 10 will be described.

The basic unit 10 comprises an open-top rectangular tray 11 having a pair of vertical side rails 12 and projecting inwardly from said rails 12 a raised elastomeric rib or protuberance 13. As shown in FIG. 1 such ribs 13 are spaced so as to snugly engage the walls of a conventional tissue cassette 14 therebetween. Cassette 14 has a perforate base 15 and a press-fit lid 16 adapted to snap onto cassette 14 with ribs 17 adapted to fit into slots 18 on cassette 14. Tray 11 is of any desired length so as to accept whatever number of cassettes 14 may be desired to be inserted therein. FIG. 2 shows the bottom of perforated lid 16 and the cassette engaging ribs 17 forming a part thereof.

FIGS. 3 and 4 show the means 19 to fasten one or more trays 11 superposed above another. The trays 11 have a projecting base 20 thereon designed to fit over the tops of rails 12 on an adjacent tray 11. Means 19, as best shown in FIG. 4 consists of a plurality of projecting elastomeric tabs 19 affixed to the exterior of tray 11 and extending along the longitudinal sides thereof, while interior of base 20 a mating groove 21 is provided to engage with such projecting tabs 19.

FIGS. 5 through 8 illustrate that projecting base 20 of trays 11 may be provided alternately with notches 22 and projections 23 in the manner of tongue and groove fasteners to permit securing a plurality of trays 11 in side-by-side relationship. FIGS. 5 and 6 also show a fastening cable 24 (described more fully in connection with FIGS. 7 and 8). As shown in FIG. 6 such cable 24 may be provided with a plurality of cutting projection 25 (also discussed below). A pull ring 26 is provided at the end of cable 24.

As shown in FIG. 7, cable 24 is disposed within tray 11 in a compartment 27 below the cassette holding portions 13 of tray 11. Affixed to one end of such compartment 27 is a spring 28 to which cable 24 is attached. Utilizing pull ring 26, cable 24 can be extended against the spring tension, brought across the full length of tray 11 and over any cassettes 14 therein, and held in such tensioned state by a retaining rod 29 by dropping pull ring 26 thereover. Rod 29 is pivoted at 30 to permit folding out of the way when not in use as shown in FIG. 8.

By utilizing this cable and fastening means, cassettes may be positively held within the tray 11 and the entire assembly transported for fluid processing of the tissue containing cassettes including the final wax dipping thereof. Once the wax has set, the cassettes may be readily released since the cable 24 has the cutting projections thereon which will readily tear through the wax coating releasing the cassettes therefrom. The cassettes may then be readily unsnapped from the holding projections 13. A hot wash dip of the unit to melt the remaining wax and to drain it therefrom puts the unit back into operative condition for the next set of cassettes.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A tissue cassette holder for holding at least one tissue cassette having sides, said holder comprising:
   an open-top tray for holding said at least one tissue cassette, said tray having first and second ends, a first vertical side rail spaced from a second vertical side rail, and a base;
   a first elastomeric projection projecting inwardly from said first vertical side rail;
   a second elastomeric projection projecting inwardly from said second vertical side rail, said projections being operable to frictionally engage said sides of said at least one tissue cassette to retain said at least one tissue cassette between said rails;
   a plurality of elastomeric tabs projecting outwardly from said side rails, said tabs being frictionally engagable with mating grooves on a base of another tissue cassette holder, thereby to permit stacking of a plurality of tissue cassette holders; and,
   a fastening cable connected to said first end of said tray and releasably connected to said second end of said tray for further securing said at least one tissue cassette within said tray by means of the cable extending across the full length of the tray and over said at least one tissue cassette therein.

2. The tissue cassette holder of claim 1, further comprising a spring interposed between said cable and said tray.

3. The tissue cassette holder of claim 2, further comprising at least one projection extending outwardly from one side of said base, and at least one notch formed on the opposite side of said base, said at least one projection being releasably engagable to said at least one notch on the base of another tissue cassette holder, thereby to permit coupling of a plurality of tissue cassette holders in a side-by-side relationship.

4. The tissue cassette holder of claim 3, and further comprising a plurality of cutting projections extending outwardly from said cable, said projections being operable to cut wax.

* * * * *